United States Patent [19]

Naka et al.

[11] Patent Number: 5,196,444
[45] Date of Patent: Mar. 23, 1993

[54] 1-(CYCLOHEXYLOXYCARBONYLOX-Y)ETHYL 2-ETHOXY-1-[[2'-(1H-TETRAZOL-5-YL)BIPHENYL-4-YL]METHYL]BEN-ZIMIDAZOLE-7-CARBOXYLATE AND COMPOSITIONS AND METHODS OF PHARMACEUTICAL USE THEREOF

[75] Inventors: Takehiko Naka, Kobe; Kohei Nishikawa, Kyoto; Takeshi Kato, Higashiosaka, all of Japan

[73] Assignee: Takeda Chemical Industries, Ltd., Osaka, Japan

[21] Appl. No.: 687,238

[22] Filed: Apr. 18, 1991

[30] Foreign Application Priority Data

| Apr. 27, 1990 [JP] | Japan | 2-113148 |
| May 30, 1990 [JP] | Japan | 2-141942 |
| Aug. 6, 1990 [JP] | Japan | 2-208662 |
| Oct. 1, 1990 [JP] | Japan | 2-264579 |
| Dec. 24, 1990 [JP] | Japan | 2-413679 |

[51] Int. Cl.$^5$ .................... C07D 257/04; A61K 31/41
[52] U.S. Cl. ..................... 514/381; 548/253; 548/252
[58] Field of Search .................. 514/381; 548/253

[56] References Cited

U.S. PATENT DOCUMENTS

| 4,526,896 | 7/1985 | Schevrel et al. | 548/253 |
| 4,764,623 | 8/1988 | Kees | 548/253 |
| 4,775,679 | 6/1988 | Chang | 548/253 |
| 4,880,804 | 11/1989 | Carini et al. | 514/381 |

FOREIGN PATENT DOCUMENTS

| 0028833 | 5/1981 | European Pat. Off. |
| 0028834 | 5/1981 | European Pat. Off. |
| 0245637 | 11/1987 | European Pat. Off. |
| 0253310 | 1/1988 | European Pat. Off. |
| 0291969 | 11/1988 | European Pat. Off. |
| 0323841 | 7/1989 | European Pat. Off. |
| 0392317 | 10/1990 | European Pat. Off. |
| 0400835 | 12/1990 | European Pat. Off. |

*Primary Examiner*—David B. Springer
*Attorney, Agent, or Firm*—Wegner, Cantor, Mueller & Player

[57] ABSTRACT

1-(Cyclohexyloxycarbonyloxy)ethyl 2-ethoxy-1-[[2'-(1H-tetrazol-5-yl)biphenyl-4-yl]methyl]benzimidazole-7-carboxylate or a pharmaceutically acceptable salt thereof has potent angiotensin II antihypertensive activity, thus being useful as therapeutic agents for treating circulatory system diseases such as hypertensive diseases, heart diseases (e.g. hypercardia, heart failure, cardiac infarction, etc.), strokes, cerebral apoplexy, nephritis, etc.

9 Claims, 3 Drawing Sheets

1-(CYCLOHEXYLOXYCARBONYLOXY)ETHYL 2-ETHOXY-1-[[2'-(1H-TETRAZOL-5-YL)BIPHENYL-4-YL]METHYL]BENZIMIDAZOLE-7-CARBOXYLATE AND COMPOSITIONS AND METHODS OF PHARMACEUTICAL USE THEREOF

SUMMARY OF THE INVENTION

In a first aspect of the invention there is provided 1-(cyclohexyloxycarbonyloxy)ethyl 2-ethoxy-1-[[2'-(1H-tetrazol-5-yl)biphenyl-4-yl]methyl]benzimidazole-7-carboxylate, including certain stable forms as well as pharmaceutically acceptable salts, which have Potent anti-hypertensive activity and strong angiotensin II antagonistic action, which are of practical value in clinical use as therapeutic agents.

These compounds possess highly angiotensin II receptor antagonistic activity as well as exerting strong oral and long-lasting angiotensin II antagonistic and anti-hypertensive action.

These compounds are unexpectedly potent angiotensin II antagonists which are of value in the treatment of circulatory system diseases such as hypertensive diseases, heart diseases, strokes, nephritis, etc.

Another aspect of the present invention relates to pharmaceutical compositions comprising an effective amount of the 1-(cyclohexyloxycarbonyloxy)ethyl 2-ethoxy-1-[[2'-(1H-tetrazol-5-yl)biphenyl-4-yl]methyl]benzimidazole-7-carboxylate and a pharmaceutically acceptable carrier useful in treating circulatory system diseases such as hypertensive diseases, heart diseases, strokes, renal failure, nephritis, etc., and processes for preparing such compounds and compositions.

Still another aspect of the present invention relates to a method for treating said circulatory system diseases of animals, which comprises administering an effective amount of the 1-(cyclohexyloxycarbonyloxy)ethyl 2-ethoxy-1-[[2'-(1H-tetrazol-5-yl)biphenyl-4-yl]methyl]benzimidazole-7-carboxylate or the pharmaceutical composition thereof to said animal.

In a still further aspect of the invention, a method is provided for producing 1-(cyclohexyloxycarbonyloxy)ethyl 2-ethoxy-1-[[2'-(1H-tetrazol-5-yl)biphenyl-4-yl]methyl]benzimidazole-7-carboxylate which comprises contacting cyclohexyl 1-iodoethyl carbonate with 2-ethoxy-1-[[2'-(1H-tetrazol-5-yl)biphenyl-4-yl]methyl]benzimidazole-7-carboxylic acid under conditions permitting esterification.

DETAILED DESCRIPTION OF THE INVENTION

Figure 1:
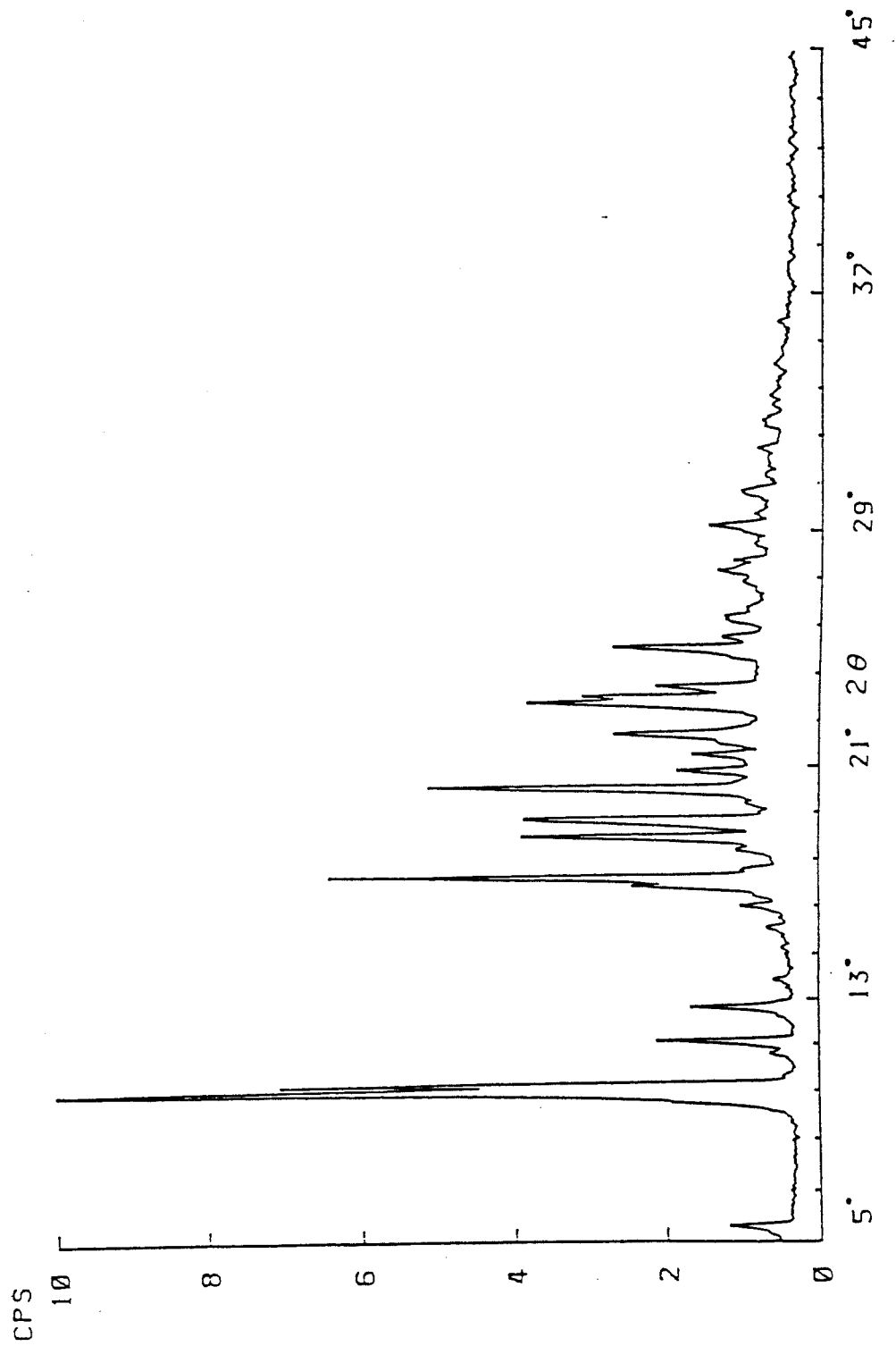
FIG. 1 depicts a X ray scattering chart obtained in Experimental Example 1.

The present invention provides 1-(cyclohexyloxycarbonyloxy)ethyl 2-ethoxy-1-[[2'-(1H-tetrazol-5-yl)biphenyl-4-yl]methyl]benzimidazole-7-carboxylate and the pharmaceutically acceptable salts thereof, which possess strong angiotensin II antagonist activity and are of value in the treatment of circulatory diseases such as hypertensive diseases, heart diseases, strokes, cerebral diseases, nephritis, etc., pharmaceutical compositions comprising an effective amount of 1-(cyclohexyloxycarbonyloxy)ethyl 2-ethoxy-1-[[2'-(1H-tetrazol-5-yl)biphenyl-4-yl]methyl]benzimidazole-7-carboxylate and a pharmaceutically acceptable carrier useful in treating said circulatory diseases, and processes for preparing such compounds and compositions.

When the compounds of the present invention have several asymmetric carbon atoms, they can thus exist in several stereochemical forms. The invention includes the mixture of isomers and the individual stereoisomers. It is intended that the present invention includes geometrical isomers, rotational isomers, enantiomers, racemates, and diastereomers.

Pharmaceutically acceptable salts of 1-(cyclohexyloxycarbonyloxy)ethyl 2-ethoxy-1-[[2'-(1H-tetrazol-5-yl)biphenyl-4-yl]methyl]benzimidazole-7-carboxylate can be formed as salts with non-toxic, physiologically or pharmaceutically acceptable acids or bases, for example salts with an inorganic acid such as hydrochloride, sulfate or nitrate, and, depending on compounds, salts with an organic acid such as acetate, oxalate, succinate or maleate, salts with an alkali metal such as sodium salt or potassium salt, or salts with an alkaline earth metal such as calcium salt.

The compounds and the salts thereof thus produced are less toxic, strongly inhibit the vasoconstrictive and hypertensive actions of angiotension II, exert a hypotensive effect in animals, in particular mammals (e.g. human, dog, rabbit, rat, etc.), and therefore they are useful as therapeutics for not only hypertension but also circulatory diseases such as heart failure (hypertrophy of the heart, cardiac insufficiency, cardiac infarction or the like), strokes, cerebral apoplexy, nephropathy and nephritis. 1-(Cyclohexyloxycarbonyloxy)ethyl 2-ethoxy-1-[[2'-(1H-tetrazol-5-yl)biphenyl-4-yl]methyl]benzimidazole-7-carboxylate and salts thereof according to the present invention strongly inhibit vasoconstriction and hypertension derived by angiotensin II and therefore possess potent anti-hypertensive activity in animals, more specifically mammal animals (e.g. humans, dogs, pigs, rabbits, rats, etc.). Further, 1-(cyclohexyloxycarbonyloxy)ethyl 2-ethoxy-1-[[2'-(1H-tetrazol-5-yl)biphenyl-4-yl]methyl]benzimidazole-7-carboxylate and salts thereof according to the present invention are of quite low toxicity and clinically useful in treating not only hypertension but also circulatory system diseases such as heart and brain diseases, strokes, renal failures, nephritis and the like.

For therapeutic use, 1-(cyclohexyloxycarbonyloxy)ethyl 2-ethoxy-1-[[2'-(1H-tetrazol-5-yl)biphenyl-4-yl]methyl]benzimidazole-7-carboxylate and salts thereof can be orally, parenterally, by inhalation spray, rectally, or topically administered as pharmaceutical compositions or formulations (e.g. powders, granules, tablets, pills, capsules, injections, syrups, emulsions, elixirs, suspensions, solutions and the like) comprising at least one such compound alone or in admixture with pharmaceutically acceptable carriers, adjuvants, vehicles, excipients and/or diluents. The pharmaceutical compositions can be formulated in accordance with conventional methods. The term parenteral as used herein includes subcutaneous injections, intravenous, intramuscular, intraperitoneal injections, or infusion techniques. Injectable preparations, for example, sterile injectable aqueous or oleaginous suspensions may be formulated according to the known art using suitable dispersing or wetting agents and suspending agents.

The sterile injectable preparation may also be a sterile injectable solution or suspension in a non-toxic parenterally acceptable diluent or solvent, for example, as a solution in water. Among the acceptable vehicles or solvents that may be employed are water, Ringer's solution, and isotonic sodium chloride solution. In addition, sterile, fixed oils are conventionally employed as a solvent or suspending medium. For this purpose any bland fixed oil or fatty acid may be employed including natural, synthetic, or semi-synthetic fatty oils or acids, and natural, synthetic, or semi-synthetic mono-, di-, or triglycerides.

Suppositories for rectal administration of the drug can be prepared by mixing the drug with a suitable non-irritating excipient such as cocoa butter and polyethylene glycols which are solid at ordinary temperatures but liquid at the rectal temperature and will therefore melt in the rectum and release the drug. Solid dosage forms for oral administration may include powders, granules, tablets, pills, and capsules as mentioned above. In such solid dosage forms, the active compound may be admixed with at least one additive such as sucrose, lactose, celluloses, mannitol, maltitol, dextran, starches, agars, alginates, chitins, chitosans, pectins, tragacanth gums, arabic gums, gelatins, collagens, casein, albumin, and synthetic or semi-synthetic polymers or glycerides. Such dosage forms may also comprise, as is normal practice, additional substances other than inert diluents, e.g., lubricating agents as magnesium stearate, preservatives such as parabens and sorbic acid, antioxidants such as ascorbic acid, α-tocopherol and cysteine, disintegrants, binders, thickening, buffering, sweetening, flavoring, and perfuming agents. Tablets and pills can additionally be prepared with enteric coatings. Liquid dosage forms for oral administration may include pharmaceutically acceptable emulsions, syrups, elixirs, suspensions, solutions containing inert diluents commonly used in the art, such as water.

Specific dose levels for any particular patient will be employed depending upon a variety of factors including the activity of specific compounds employed, the age, body weight, general health, sex, diet, time of administration, route of administration, rate of excretion, drug combination, and the severity of the particular disease undergoing therapy. The dose varies with the diseases to be treated, symptoms, subjects and administration routes, and it is desirable that a daily dose of 1 to 50 mg for oral administration or 1 to 30 mg for intravenous injection can be administered in single or divided into 2 to 3 administrations when used as an agent for the therapy in adults. For example, when used for treating adult essential hypertension, the active ingredient will preferably be administered in an appropriate amount, for example, about 10 mg to 100 mg a day orally and about 5 mg to 50 mg a day intravenously. The active ingredient will preferably be administered in equal doses two or three times a day.

The foregoing is merely illustrative of the invention and is not intended to limit the invention to the disclosed compounds.

EXAMPLES

By the following formulation examples, working examples, experimental examples and reference examples, the present invention will be explained more concretely, but they should not be interpreted as limiting the invention in any manner.

Examples of abbreviations in this specification are as follows:

Me: methyl, Et: ethyl, Tet: tetrazolyl, cycl: cyclo-, Pr: propyl, Bu: butyl, Pen: pentyl, Bu: butyl, Hex: hexyl, Hep: heptyl, Ph: phenyl, DMF: dimethylformamide, and THF: tetrahydrofuran.

FORMULATION EXAMPLES

When 1-(cyclohexyloxycarbonyloxy)ethyl 2-ethoxy-1-[[2'-(1H-tetrazol-5-yl)biphenyl-4-yl]methyl]-benzimidazole-7-carboxylate of the present invention is used as a therapeutic agent for circulatory failures such as hypertension, heart diseases, strokes, kidney diseases, etc., it can be used in accordance with, for example, the following formulations.

| 1. Capsules | |
|---|---|
| (1) 1-(cyclohexyloxycarbonyloxy)ethyl 2-ethoxy-1-[[2'-(1H-tetrazol-5-yl)biphenyl-4-yl]methyl]benzimidazole-7-carboxylate | 10 mg |
| (2) lactose | 90 mg |
| (3) fine crystalline cellulose | 70 mg |
| (4) magnesium stearate | 10 mg |
| one capsule | 180 mg |

(1), (2), (3) and a half of (4) are mixed and granulated. To the granules is added the remainder of (4), and the whole is filled into gelatin capsules.

| 2. Tablets | |
|---|---|
| (1) 1-(cyclohexyloxycarbonyloxy)ethyl 2-ethoxy-1-[[2'-(1H-tetrazol-5-yl)biphenyl-4-yl]methyl]benzimidazole-7-carboxylate | 10 mg |
| (2) lactose | 35 mg |
| (3) corn starch | 150 mg |
| (4) fine crystalline cellulose | 30 mg |
| (5) magnesium stearate | 5 mg |
| one tablet | 230 mg |

(1), (2), (3), two thirds of (4) and a half of (5) are mixed and granulated. To the granules are added the remainders of (4) and (5), followed by subjecting the granules to compression molding.

REFERENCE EXAMPLE 1

Ethyl 2-carboxy-3-nitrobenzoate

A mixture of 3-nitrophthalic acid (35 g) in ethanol (300 ml) containing conc. sulfuric acid (20 ml) was heated under reflux for 24 hours. The solvent was evaporated in vacuo and the residue was poured into cold water (700 ml). The mixture was extracted with ethyl acetate. The organic layer was washed with water and shaken with an aqueous solution of potassium carbonate. The aqueous layer was made acidic with hydrochloric acid and the mixture was extracted with methylene chloride. The organic layer was washed with water, then dried, followed by evaporation of the solvent. The resultant solid (29 g, 74%) was used for the subsequent reaction without purification.

$^1$H-NMR(90 MHz, CDCl$_3$) δ : 1.43(3H,t), 4.47(2H,q), 7.70(1H,t), 8.40(2H,d), 9.87(1H,br s)

IR(Nujol) cm$^{-1}$: 1725, 1535, 1350, 1300, 1270

REFERENCE EXAMPLE 2

Ethyl 2-t-butoxycarbonylamino-3-nitrobenzoate

A mixture of ethyl 2-carboxy-3-nitrobenzoate (23.9 g) and thionyl chloride (12 ml) in benzene (150 ml) were heated under reflux for 3 hours. The reaction mixture was concentrated to dryness. The resultant acid chloride (26 g, quantitative) was dissolved in methylene chloride (20 ml). The solution was added dropwise to a mixture of sodium azide (9.75 g) in dimethylformamide(DMF) (20 ml) with stirring vigorously. The reaction mixture was poured into a mixture of ether-hexane (3:1, 200 ml) and water (250 ml) to separate into two layers. The organic layer was washed with water, then dried, followed by evaporation of the solvent. The residue was dissolved in t-butanol (200 ml) and the solution was heated gradually with stirring, followed by heating under reflux for 2 hours. The reaction mixture was concentrated in vacuo to give an oily product (30 g).

$^1$H-NMR(90 MHz, CDCl$_3$) δ : 1.40(3H,t), 1.53(9H,s), 4.43(2H,q), 7.23(1H,t), 8.03–8.27(2H,m), 9.70(1H,br s)

IR(Neat) cm$^{-1}$: 3320, 2980, 1740, 1585, 1535, 1500, 1440, 1375, 1265, 1155

WORKING EXAMPLE 1

Ethyl 2-[[2′-cyanobiphenyl)]amino]-3-nitrobenzoate

To a solution of ethyl 2-t-butoxycarbonylamino-3-nitrobenzoate (20 g) in tetrahydrofuran (50 ml) was added, while stirring under ice-cooling, sodium hydride (60% dispersion in mineral oil, 2.8 g). The mixture was stirred at room temperature for 20 minutes and to the mixture were then added 4-(2-cyanophenyl)benzyl bromide (18 g) and potassium iodide (360 mg), followed by heating for 10 hours under reflux. The solvent was evaporated to dryness and the residue was partitioned between water (250 ml) and ether (200 ml). The organic layer was washed with water, dried and concentrated to give a yellow syrup. The syrup was dissolved in a mixture of trifluoroacetic acid (60 ml) and methylene chloride (40 ml) and the solution was stirred for one hour at room temperature. The reaction mixture was concentrated to dryness and to the residue was added ethyl ether (200 ml) to give crystals. The crystals were collected by filtration, washed with ether to give pale yellow crystals (22.1 g, 85%), m.p. 118°–119° C.

$^1$H-NMR(90 MHz, CDCl$_3$) δ : 1.37(3H,t), 4.23(2H,s), 4.37(2H,q), 6.37(1H,t), 7.33–7.83(9H,m), 7.97–8.20(2H,m)

IR(Nujol)cm$^{-1}$: 3280, 2220, 1690, 1575, 1530, 1480, 1450, 1255, 1105, 755

WORKING EXAMPLE 2

Ethyl 3-amino-2-[[2′-cyanobiphenyl-4-yl)methyl]amino]benzoate

To a solution of ethyl 2-[[(2′-cyanobiphenyl-4-yl)methyl]amino]nitrobenzoate (10.4 g) in ethanol (50 ml) was added stannous dichloride dihydrate (28.1 g) and the mixture was stirred at 80° C. for two hours. The solvent was evaporated to dryness. To the ice-cooling mixture of the residue in ethyl acetate (300 ml) was added dropwise 2N NaOH (500 ml) with stirring. The aqueous layer was extracted with ethyl acetate (200 ml×2). The organic layers were combined, washed with water, and dried. The solvent was evaporated to dryness and the residue was purified by column chromatography on silica gel to give crystals. Recrystallization from ethyl acetate-hexane gave colorless crystals (7.3 g, 79%), m.p. 104°–105° C.

$^1$H-NMR(200 MHz, CDCl$_3$) δ : 1.33(3H,t), 4.23(2H,s), 4.27(2H,q ), 6.83–6.93(2H,m), 7.35–7.55(7H,m), 7.64(1H,dt), 7.76(dd)

IR(KBr) cm$^{-1}$: 3445, 3350, 2220, 1680, 1470, 1280, 1240, 1185, 1160, 1070, 1050, 1020, 805, 750

WORKING EXAMPLE 3

Ethyl 1-[(2′-cyanobiphenyl-4-yl)methyl]-2-ethoxybenzimidazole-7-carboxylate

Acetic acid (0.2 g) was added to a solution of ethyl 3-amino-2-N-[2′-cyanobiphenyl-4-yl)methyl]aminobenzoate (1.0 g) in ethyl orthocarbonate (5 ml). The mixture was stirred at 80° C. for one hour. The reaction mixture was concentrated, and the concentrate was dissolved in ethyl acetate. The solution was washed with an aqueous solution of sodium hydrogen carbonate and water. The solvent was evaporated to give crystals. Recrystallization from ethyl acetate-benzene afforded colorless crystals (0.79 g, 69%), m.p. 131°–132° C.

| Elemental Analysis for C$_{26}$H$_{23}$N$_3$O$_3$: | | |
|---|---|---|
| C (%) | H (%) | N (%) |
| Calcd.: 73.39; | 5.45; | 9.88 |
| Found: 73.36; | 5.42 | 9.83 |

$^1$H-NMR(200 MHz, CDCl$_3$) δ : 1.24(3H,t), 1.49(3H,t), 4.24(2H,q), 4.68(2H,q), 5.72(2H,s), 7.10(2H,d), 7.19(1H,t), 7.38–7.46(4H,m), 7.56–7.66(2H,m), 7.73–7.77(2H,m)

IR(KBr) cm$^{-1}$: 2220, 1720, 1550, 1480, 1430, 1280, 1245, 1215, 1040, 760, 740

WORKING EXAMPLE 4

Ethyl 2-ethoxy-1-[[2′-(1H-tetrazol-5-yl)biphenyl-4-yl]-methyl]benzimidazole-7-carboxylate A mixture of ethyl 1-[(2′-cyanobiphenyl-4-yl)methyl]-2-ethoxybenzimidazole-7-carboxylate (0.7 g) and trimethyltin azide (0.7 g) in toluene (15 ml) was heated under reflux for 4 days. The reaction mixture was concentrated to dryness and to the residue were added methanol (20 ml) and 1N-HCl (10 ml). The mixture was stirred at room temperature for 30 minutes and adjusted to pH 3 to 4 with 1N NaOH. After removal of the solvent, the residue was partitioned between chloroform and water. The organic layer was washed with water and dried, and the solvent was evaporated to dryness to give a syrup. The syrup was purified by column chromatography on silica gel to give crystals. Recrystallization from ethyl acetate-benzene afforded colorless crystals (0.35 g, 45%), m.p. 158°–159° C.

| Elemental Analysis for C$_{26}$H$_{24}$N$_6$O$_3$: | | |
|---|---|---|
| C (%) | H (%) | N (%) |
| Calcd.: 66.65; | 5.16; | 17.94 |
| Found: 66.61; | 5.05; | 17.84 |

$^1$H-NMR(200 MHz,CDCl$_3$) δ : 1.09(3H,t), 1.43(3H,t), 4.02(2H,q), 4.30(2H,q), 5.57(2H,s), 6.71(2H,d), 6.83–6.96(4H,m), 7.27–7.31(1H,m), 7.40(1H,dd), 7.55–7.66(2H,m), 8.04–8.09(1H,m)

IR(KBr) cm$^{-1}$: 1720, 1605, 1540, 1470, 1430, 1250, 1040, 750

WORKING EXAMPLE 5

2-Ethoxy-1-[[2'-(1H-tetrazol-5-yl)biphenyl-4-yl]methyl]-benzimidazole-7-carboxylic acid A solution of ethyl 2-ethoxy-1-[[2'-(1H-tetrazol-5-yl)-biphenyl-4-yl]methyl]benzimidazole-7-carboxylate (0.24 g) and 1N NaOH (1.5 ml) in ethanol (4 ml) was stirred at 80° C. for one hour. The reaction mixture was concentrated, and the concentrate was extracted with water and ethyl acetate. The aqueous layer was adjusted to pH 3-4 with 1N-HCl to give crystals. Recrystallization of the crystals from ethyl acetate-methanol afforded colorless crystals (0.15 g, 67%), m.p. 183°-185° C.

| Elemental Analysis for $C_{24}H_{20}N_6O_3 \cdot 1/5H_2O$: | | | |
|---|---|---|---|
| | C (%) | H (%) | N (%) |
| Calcd.: | 64.91; | 4.63; | 18.93 |
| Found: | 65.04; | 4.51; | 18.77 |

$^1$H-NMR(200 MHz,DMSO-$d_6$) δ : 1.38(3H,t), 4.58(2H,q), 5.63(2H,s), 6.97(4H,q), 7.17(1H,t), 7.47-7.68(6H,m)

IR(KBr) cm$^{-1}$: 1710, 1550, 1480, 1430, 1280, 1240, 1040, 760

WORKING EXAMPLE 6

2-Ethoxy-1-[[2'-(N-triphenylmethyltetrazol-5-yl)-biphenyl-4-yl]methyl]benzimidazole-7-carboxylic acid To a solution of 2-ethoxy-[[2'-(1H-tetrazol-5-yl)biphenyl-4-yl]methyl]benzimidazole-7-carboxylic acid (2.07 g) in methylene chloride (10 ml) were added trityl chloride (1.59 g) and triethylamine (0.8 ml). The mixture was stirred at room temperature for one hour. The reaction mixture was washed with water, dried and concentrated to dryness. The residue was purified by column chromatography on silica gel to give crystals. Recrystallization of crude crystals thus obtained from ethyl acetate-benzene gave colorless crystals (2.12 g, 66%), m.p. 168°-170° C.

| Elemental Analysis for $C_{43}H_{34}N_6O_3$: | | | |
|---|---|---|---|
| | C (%) | H (%) | N (%) |
| Calcd.: | 75.64; | 5.02; | 12.31 |
| Found: | 75.37; | 4.96; | 12.20 |

$^1$H-NMR(200 MHz, CDCl$_3$) δ : 1.40(3H,t), 4.61(2H,q), 5.58(2H,s), 6.76(2H,d), 6.91-6.96(8H,m), 7.12(1H,t), 7.17-7.41(12H,m), 7.60(1H,dd), 7.73-7.82(2H,m)

WORKING EXAMPLE 7

1-(Cyclohexyloxycarbonyloxy)ethyl 2-ethoxy-1-[[2'-(1H-tetrazol-5-yl)biphenyl-4-yl]methyl]-benzimidazole-7-carboxylate To a solution of 2-ethoxy-1-[[2'-(N-triphenylmethyltetrazol-5-yl)biphenyl-4-yl]methyl]benzimidazole-7-carboxylic acid (0.5 g) in DMF (5 ml) were added potassium carbonate (0.12 g) and cyclohexyl 1-iodoethyl carbonate (0.26 g). The mixture was stirred for one hour at room temperature. To the reaction mixture was added water and the mixture was extracted with ethyl acetate. The organic layer was washed with water and dried. After removal of the solvent, the residue was dissolved in methanol (10 ml) and to the solution was added 1N-HCl (2 ml). The mixture was stirred for one hour at room temperature. The reaction mixture was concentrated to dryness and the residue was partitioned between ethyl acetate and water. The organic layer was washed with water and dried. After removal of the solvent, the residue was purified by column chromatography on silica gel to give colorless powder (0.21 g, 47%), m.p. 103°-106° C.

| Elemental Analysis for $C_{33}H_{34}N_6O_6$: | | | |
|---|---|---|---|
| | C (%) | H (%) | N (%) |
| Calcd.: | 64.91; | 5.61; | 13.76 |
| Found: | 64.94; | 5.71; | 13.66 |

To the powder (1 g) obtained as above was added ethanol (6 ml). The mixture was stirred for 3 hours at room temperature and allowed to stand under ice-cooling. The mixture was then stirred for one hour at temperatures not higher than 10° C. Resultant crystals were collected by filtration and washed with cold ethanol. The crystals were dried at 25° C. for 9 hours under reduced pressure, then at 35° C. for further 18 hours to obtain white powdery crystals (0.94 g), m.p. 158°-166° C. (decomp.).

| Elemental Analysis for $C_{33}H_{34}N_6O_6$: | | | |
|---|---|---|---|
| | C (%) | H (%) | N (%) |
| Calcd.: | 64.91; | 5.61; | 13.76 |
| Found: | 64.73; | 5.66; | 13.64 |

$^1$H-NMR (200 MHz) δ : 1.13-1.84(16H,m), 4.28-4.55(3H,m), 5.65(2H,d), 6.72(1H,q), 6.81(2H,d), 6.93(2H,d), 7.03(1H,t), 7.22-7.23(1H,m), 7.31-7.36(1H,m), 7.52-7.60(3H,m), 8.02-8.07(1H,m)

IR(KBr) cm$^{-1}$: 2942, 1754, 1717, 1549, 1476, 1431, 1076, 1034, 750 MS(m/z): 611 [M+H]$^+$

EXPERIMENTAL EXAMPLE 1

Figure 2:
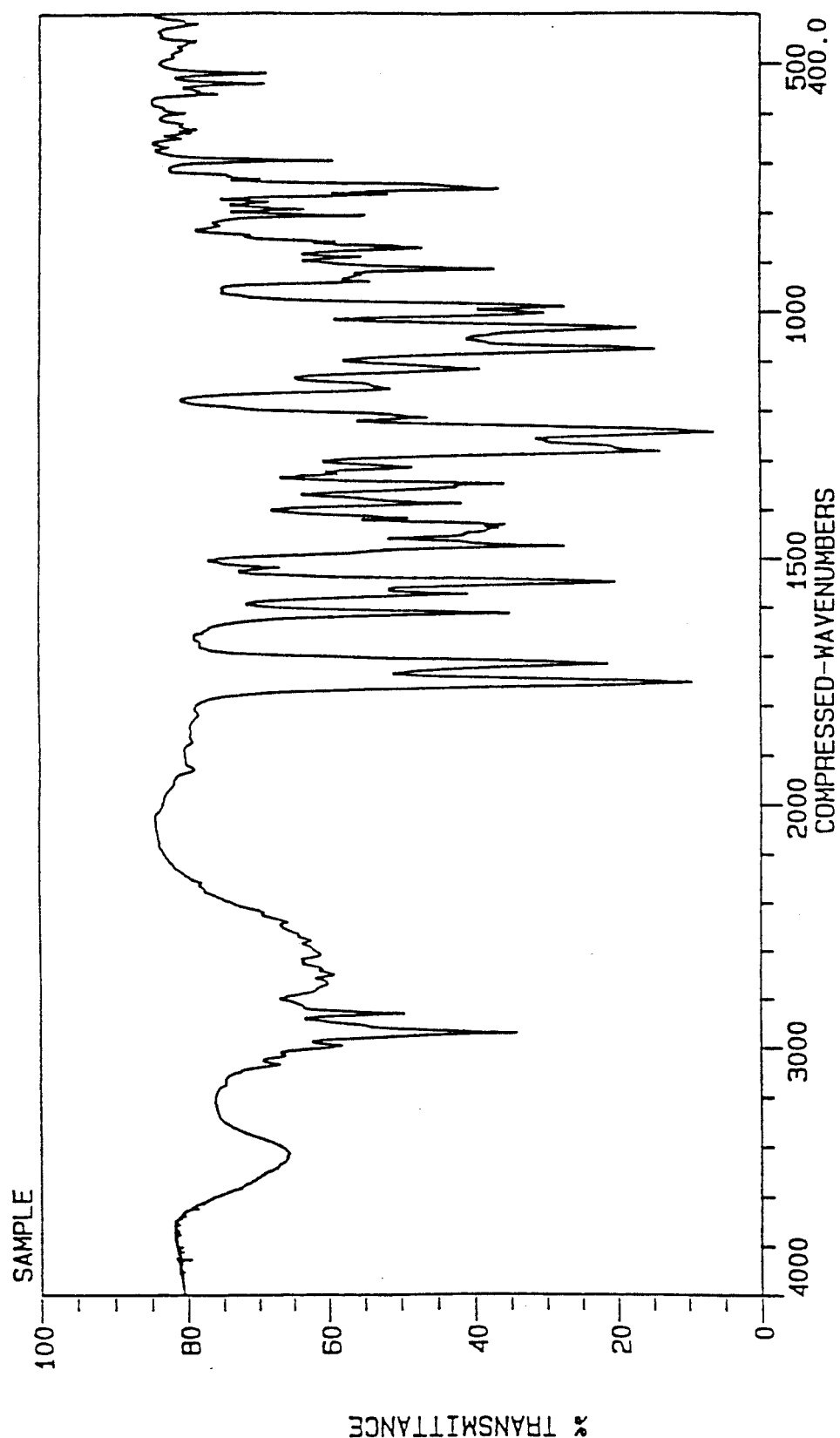
FIG. 2 depicts an IR spectrum pattern obtained in Experimental Example 1.
Figure 3:
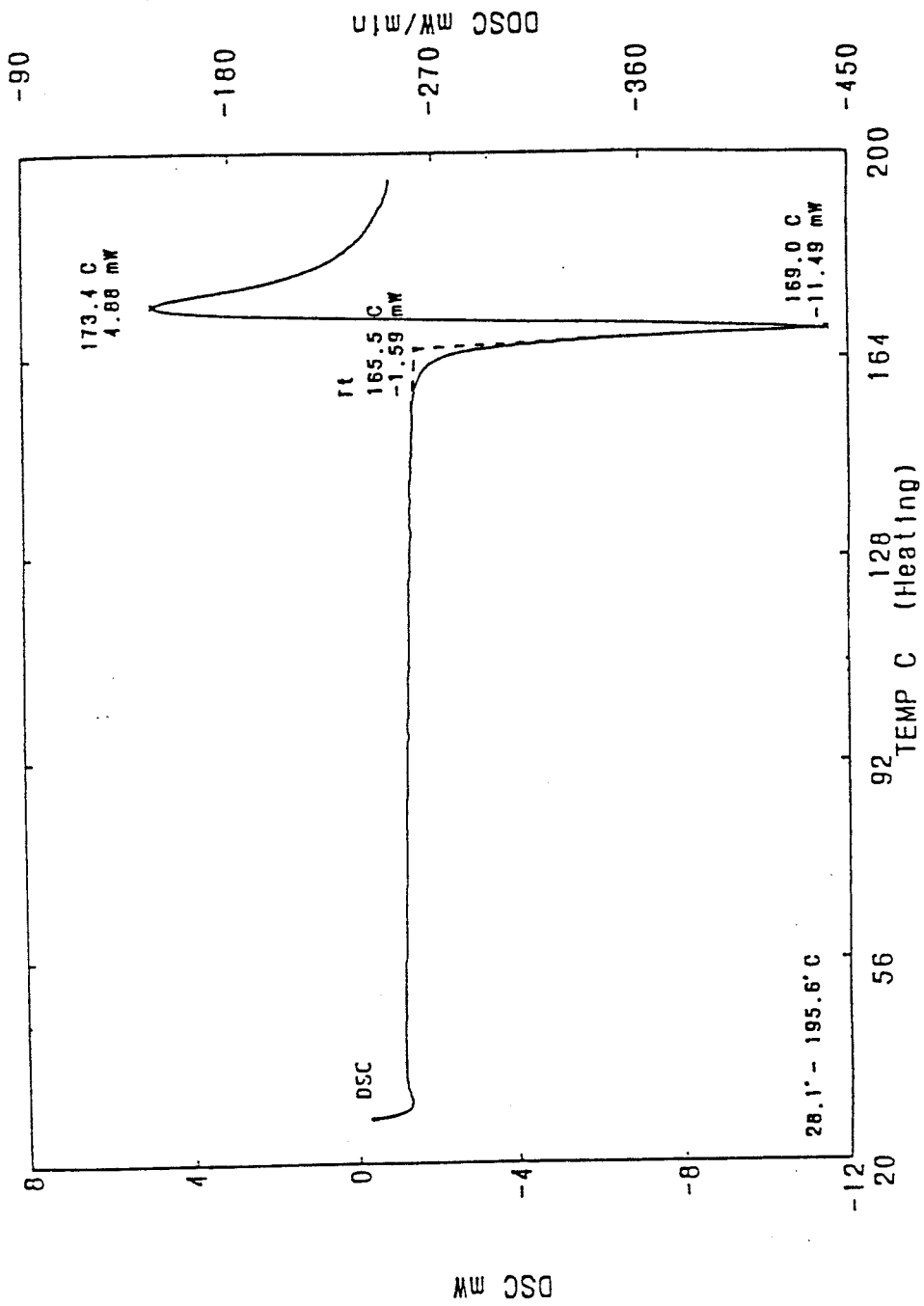
FIG. 3 depicts a differential scanning calorimeter pattern obtained in Experimental Example 1.

Stable C-type crystalline 1-(cyclohexyloxycarbonyloxy)ethyl 2-ethoxy-1-[[2'-(1H-tetrazol-5-yl)biphenyl-4-yl]methyl]-benzimidazole-7-carboxylate and preparation thereof 1-(Cyclohexyloxycarbonyloxy)ethyl 2-ethoxy-1-[[2'-(1H-tetrazol-5-yl)biphenyl-4-yl]methyl]benzimidazole-7-carboxylate is usually purified by column chromatography on silica gel and the eluted fraction is concentrated to dryness to give amorphous powders. The powder is unstable by heat and impractical in production. For solving this problem, the present inventors made extensive experiments on crystallization of the subject compound and discovered C-type crystalline form. The C-type crystal is unexpectedly stable by heat and quite useful for production. The C-type crystal of the title compound has approximately the following lattice spacings:

3.5 angstrom; middle
3.7 angstrom; weak
3.8 angstrom; middle
4.0 angstrom; middle
4.1 angstrom; weak
4.3 angstrom; weak
4.4 angstrom; middle
4.6 angstrom; middle
4.8 angstrom; middle
5.1 angstrom; middle 5.2 angstrom; weak
6.9 angstrom; weak
7.6 angstrom; weak
8.8 angstrom; middle
9.0 angstrom; strong
15.9 angstrom; weak IR spectrum (KBr tablet) of the C-type crystal is shown in FIG. 2 with the significant absorption maxima at 2942, 1754, 1717, 1615, 1549, 1476 and 750 cm$^{-1}$ and its melting point is 158°–166° C. (decomposition). Representative X ray chart (powder method), IR spectra (KBr tablet) and differential scanning calorimeter patterns are shown in FIGS. 1–3, respectively.

The C-type crystal of 1-(cyclohexyloxycarbonyloxy)ethyl-2-ethoxy-1-[[2'-(1H-tetrazol-5-yl)biphenyl-4-yl]methyl]-benzimidazole-7-carboxylate has advantages, for example;

1. It improves heat stability and practical utility.
2. Residual solvent can be minimized in crystals.
3. It can achieve industrial and clinical developments and give ecomomical benefits.

The concentrated residues, amorphous powders, and/or crystals except for the C-type crystal for obtaining the subject compound, are stirred in a suitable solvent to form the desired C-type crystal. In case where the C-type crystal is not formed, a small amount of the C-type crystal can be added as a seed to allow crystallization. Examples of such solvents are not limited to, as long as they afford the C-type crystal, but include lower alcohols (e.g. methanol, ethanol, isopropyl alcohol, etc.), a mixture of lower alcohol and water and a mixture of lower alkyl ketone (e.g. acetone, etc.) and water. Amounts of solvents used are not limited to, but practically, 2 to 30-fold per weight of the crystal. Ratios of lower alcohol vs. water and lower alkyl ketone vs. water are not limited to, but preferably 4:1 to 1:1. Stirring temperatures are not limited to, but −5° C. to 40° C., preferably 0° C. to 25° C.

EXPERIMENTAL EXAMPLE 2

Inhibition of binding of angiotensin II to angiotensin receptor

Method

An experiment of inhibition on the binding of angiotensin II (AII) to AII receptor was conducted by modifying the method of Douglas et al. [Endocrinology, 102, 685–696 (1978)]. An AII receptor membrane fraction was prepared from bovine adrenal cortex.

The compound of the present invention ($10^{-6}$M or $10^{-7}$M) and $^{125}$I-angiotensinII ($^{125}$I-AII) (1.85 kBq/50 μl) were added to the receptor membrane fraction, and the mixture was incubated at room temperature for one hour. The receptor-bound and free $^{125}$I-AII were separated through a filter (Whatman GF/B filter), and the radioactivity of $^{125}$I-AII bound to the receptor was measured.

Results

The results relating to the compounds of the present invention are shown in Table 2.

EXPERIMENTAL EXAMPLE 3

Inhibitory effect of the compound of the present invention on pressor action of AII Method Jcl: SD rats (9 week old, male) were employed. On the previous day of the experiment, these animals were applied with cannulation into the femoral artery and vein under anesthesia with pentobarbital Na. The animals were fasted but allowed to access freely to drinking water until the experiment was started. Just on the day of conducting the experiment, the artery cannula was connected with a blood-pressure transducer, and the average blood pressure was recorded by means of polygraph. Before administration of the drug, the pressor action due to intravenous administration of AII (100 ng/kg) as the control was measured. The drugs were orally administered, then, at each point of the measurement, AII was administered intravenously, and the pressor action was similarly measured. By comparing the pressor action before and after administration of the drug, the percent inhibition by the drug on AII-induced pressor action was evaluated.

Results

The results relating to the compounds of the present invention are shown in Table 2.

TABLE 2

| Working Example No. | Radioreceptor Assay | | Pressor Response to A II (p.o.) |
|---|---|---|---|
| | $1 \times 10^{-7}$ M | $1 \times 10^{-6}$ M | 3 mg/kg |
| 4 | 46 | 82 | +++ a) |
| 5 | 61 | 91 | +++ |
| 7 | 32 | 77 | +++ | a) +++ ≧ 70% > ++ ≧ 50% > + ≧ 30% > −

The foregoing is merely illustrative of the invention and is not intended as limiting the scope of the invention which is defined by the following claims:

What is claimed is:

1. A stable crystal of 1-(cyclohexyloxycarbonyloxy)ethyl 2-ethoxy-1-[[2'-(1H-tetrazol-5-yl)-biphenyl-4-yl]methyl]benzimidazole-7-carboxylate.

2. A stable crystal according to claim 1, which has approximately the following lattice spacings:
   3.5 angstrom; middle
   3.7 angstrom; weak
   3.8 angstrom; middle
   4.0 angstrom; middle
   4.1 angstrom; weak
   4.3 angstrom; weak
   4.4 angstrom; middle
   4.6 angstrom; middle
   4.8 angstrom; middle
   5.1 angstrom; middle
   5.2 angstrom; weak
   6.9 angstrom; weak
   7.6 angstrom; weak
   8.8 angstrom; middle
   9.0 angstrom; strong
   15.9 angstrom; weak.

3. A pharmaceutical composition for antagonizing angiotensin II which comprises a therapeutically effective amount of 1-(cyclohexyloxycarbonyloxy)ethyl 2-ethoxy-1-[[2'-(1H-tetrazol-5-yl)biphenyl-4-yl]methyl]-benzimidazole-7-carboxylate or a pharmaceutically acceptable salt thereof in admixture with a pharmaceutically acceptable carrier, excipient or diluent therefor.

4. A pharmaceutical composition for antagonizing angiotensin II which comprises a therapeutically effective amount of a crystal according to claim 1 in admixture with a pharmaceutically acceptable carrier, excipient or diluent therefor.

5. A pharmaceutical composition for antagonizing angiotensin II which comprises a therapeutically effective amount of a crystal according to claim 2 in admixture with a pharmaceutically acceptable carrier, excipient or diluent therefor.

6. A method for antagonizing angiotensin II in a mammal which comprises administering to said mammal a therapeutically effective amount of 1-(cyclohexyloxycarbonyloxy)ethyl 2-ethoxy-1-[[2'-(1H-tetrazol-5-yl)biphenyl-4-yl]methyl]benzimidazole-7-carboxylate or a pharmaceutically acceptable salt thereof.

7. A method for antagonizing angiotensin II in a mammal which comprises administering to said mammal a therapeutically effective amount of a crystal according to claim 1.

8. A method for antagonizing angiotensin II in a mammal which comprises administering to said mammal a therapeutically effective amount of a crystal according to claim 2.

9. 1-(Cyclohexyloxycarbonyloxy)ethyl 2-ethoxy-1-[[2'-(1H-tetrazol-5-yl)biphenyl-4-yl]methyl]benzimidazole-7-carboxylate or a pharmaceutically acceptable salt thereof.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 5,196,444 |
| (45) | ISSUED | : | March 23, 1993 |
| (75) | INVENTORS | : | Takehiko Naka, et al. |
| (73) | PATENT OWNER | : | Takeda Chemical Industries Ltd. |
| (95) | PRODUCT | : | ATACAND® (candesartan cilexetil) |

This is to certify that an application under 35 U.S.C. § 156 has been filed in the United States Patent and Trademark Office, requesting extension of the term of U.S. Patent No. 5,196,444 based upon the regulatory review of the product ATACAND® (candesartan cilexetil) by the Food and Drug Administration. Since it appears that the requirements of the law have been met, this certificate extends the term of the patent for the period of

(94)    413 days from April 18, 2011, the original expiration date of the patent, subject to the payment of maintenance fees as provided by law, with all rights pertaining thereto as provided by 35 U.S.C. § 156(b).

I have caused the seal of the Patent and Trademark Office to be affixed this 18th day of July 2001.

Nicholas P. Godici
Acting Under Secretary of Commerce for Intellectual Property and
Acting Director of the United States Patent and Trademark Office